US 8,721,610 B2

(12) United States Patent
Langdon et al.

(10) Patent No.: US 8,721,610 B2
(45) Date of Patent: *May 13, 2014

(54) ABSORBENT ARTICLE PROVIDING A BETTER FIT AND MORE COMFORT TO A WEARER

(71) Applicant: The Procter & Gamble Company, Cincinnati, OH (US)

(72) Inventors: Frederick Michael Langdon, Cincinnati, OH (US); Uwe Schneider, Cincinnati, OH (US); Christopher Jason Hawke, Sandy Hook, CT (US); Gregory Ashton, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/707,015

(22) Filed: Dec. 6, 2012

(65) Prior Publication Data
US 2013/0096527 A1    Apr. 18, 2013

Related U.S. Application Data

(63) Continuation of application No. 12/782,016, filed on May 18, 2010, now Pat. No. 8,348,919, which is a continuation of application No. 11/169,829, filed on Jun. 29, 2005, now Pat. No. 7,744,579.

(51) Int. Cl.
*A61F 13/15* (2006.01)
*A61F 13/20* (2006.01)

(52) U.S. Cl.
USPC .................... 604/386; 604/385.27

(58) Field of Classification Search
USPC ............... 604/385.14–385.3, 385.31, 385.01
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,573,986 A | 3/1986 | Minetola et al. | |

(Continued)

FOREIGN PATENT DOCUMENTS

| | | |
|---|---|---|
| JP | 32-63659 A | 11/1991 |
| JP | 10-314225 A | 12/1998 |
| JP | 2004-232157 A | 8/2004 |
| WO | WO-95/16746 A1 | 6/1995 |

*Primary Examiner* — Michele M Kidwell
(74) *Attorney, Agent, or Firm* — Andrew J. Mueller

(57) ABSTRACT

A disposable pull-on garment has a front waist region and a back waist region opposite the front waist region. The disposable pull-on garment also has a chassis and front and back waist members attached to the chassis in the front and back waist regions, respectively. The front waist member has a first retraction force and the back waist member has a second retraction force. The disposable pull-on garment also has a pair of side members attaching the front waist region to the back waist region, thereby forming a waist opening and a pair of leg openings. Each of the pair of side members includes a waist zone and a hip zone. The waist zones have retraction forces which are about equal to the first retraction force, and the hip zones have retraction forces which are greater than the first or second retraction forces.

22 Claims, 9 Drawing Sheets

(56) References Cited

U.S. PATENT DOCUMENTS

| | | |
|---|---|---|
| 4,609,518 A | 9/1986 | Curro et al. |
| 4,610,678 A | 9/1986 | Weisman et al. |
| 4,629,643 A | 12/1986 | Curro et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,710,189 A | 12/1987 | Lash |
| 4,785,996 A | 11/1988 | Ziecker et al. |
| 4,795,278 A | 1/1989 | Hayashi |
| 4,795,454 A | 1/1989 | Dragoo |
| 4,808,178 A | 2/1989 | Aziz et al. |
| 4,834,735 A | 5/1989 | Alemany et al. |
| 4,842,666 A | 6/1989 | Werenicz |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,968,312 A | 11/1990 | Khan |
| 4,990,147 A | 2/1991 | Freeland |
| 5,006,394 A | 4/1991 | Baird |
| 5,037,416 A | 8/1991 | Allen et al. |
| 5,062,840 A | 11/1991 | Holt et al. |
| 5,092,861 A | 3/1992 | Nomura et al. |
| 5,137,537 A | 8/1992 | Herron et al. |
| 5,147,345 A | 9/1992 | Young et al. |
| 5,151,092 A | 9/1992 | Buell et al. |
| 5,171,236 A | 12/1992 | Dreier et al. |
| 5,221,274 A | 6/1993 | Buell et al. |
| 5,246,433 A | 9/1993 | Hasse et al. |
| 5,260,345 A | 11/1993 | Desmarais et al. |
| 5,269,755 A | 12/1993 | Bodicky |
| 5,269,775 A | 12/1993 | Freeland et al. |
| 5,306,266 A | 4/1994 | Freeland |
| 5,342,338 A | 8/1994 | Roe |
| 5,387,207 A | 2/1995 | Dyer et al. |
| 5,397,318 A | 3/1995 | Dreier |
| 5,415,649 A | 5/1995 | Watanabe et al. |
| 5,460,622 A | 10/1995 | Dragoo et al. |
| 5,514,121 A | 5/1996 | Roe et al. |
| 5,518,801 A | 5/1996 | Chappell et al. |
| 5,540,671 A | 7/1996 | Dreier |
| 5,554,142 A | 9/1996 | Dreier et al. |
| 5,569,234 A | 10/1996 | Buell et al. |
| 5,571,096 A | 11/1996 | Dobrin et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,653,703 A | 8/1997 | Roe et al. |
| 5,669,897 A | 9/1997 | Lavon et al. |
| 5,685,874 A | 11/1997 | Buell et al. |
| 5,735,839 A | 4/1998 | Kawaguchi et al. |
| 5,749,865 A | 5/1998 | Yamamoto et al. |
| H1732 H | 6/1998 | Johnson |
| 5,865,823 A | 2/1999 | Curro |
| 5,873,870 A | 2/1999 | Seitz et al. |
| 5,897,545 A | 4/1999 | Kline et al. |
| 5,916,206 A | 6/1999 | Otsubo et al. |
| 5,931,827 A | 8/1999 | Buell et al. |
| 5,938,648 A | 8/1999 | Lavon et al. |
| 5,941,864 A | 8/1999 | Roe |
| 5,941,865 A | 8/1999 | Otsubo et al. |
| 5,957,908 A | 9/1999 | Kline et al. |
| 5,968,025 A | 10/1999 | Roe et al. |
| 5,977,430 A | 11/1999 | Roe et al. |
| 5,997,520 A | 12/1999 | Ahr et al. |
| 6,010,490 A | 1/2000 | Freeland et al. |
| 6,013,063 A | 1/2000 | Roe et al. |
| 6,120,487 A | 9/2000 | Ashton |
| 6,120,489 A | 9/2000 | Johnson et al. |
| 6,132,411 A | 10/2000 | Huber et al. |
| 6,168,584 B1 | 1/2001 | Allen et al. |
| 6,200,299 B1 | 3/2001 | Heki |
| 6,231,558 B1 | 5/2001 | Mosley |
| 6,364,863 B1 | 4/2002 | Yamamoto et al. |
| 6,432,098 B1 | 8/2002 | Kline et al. |
| 6,478,785 B1 | 11/2002 | Ashton et al. |
| 6,595,976 B2 | 7/2003 | Jitoe et al. |
| 6,620,146 B2 | 9/2003 | Gibbs |
| 6,680,422 B2 | 1/2004 | Roe |
| 6,682,514 B1 | 1/2004 | Brunner |
| 6,692,477 B2 | 2/2004 | Gibbs |
| 6,716,441 B1 | 4/2004 | Osborne et al. |
| 6,726,699 B1 | 4/2004 | Wright et al. |
| 6,740,017 B2 | 5/2004 | Pino |
| 6,764,478 B2 | 7/2004 | Ashton et al. |
| 6,833,179 B2 | 12/2004 | May et al. |
| 6,863,666 B2 | 3/2005 | Minato |
| 7,028,735 B2 | 4/2006 | Schneider et al. |
| 7,097,710 B2 | 8/2006 | Schneider |
| 7,169,228 B2 | 1/2007 | Schneider |
| 7,201,822 B2 | 4/2007 | Schneider et al. |
| 7,222,654 B2 | 5/2007 | Schneider et al. |
| 7,291,138 B2 | 11/2007 | Hoshino et al. |
| 7,569,039 B2 | 8/2009 | Matsuda et al. |
| 7,744,579 B2 | 6/2010 | Langdon et al. |
| 2002/0002021 A1 | 1/2002 | May et al. |
| 2002/0007148 A1 | 1/2002 | May et al. |
| 2002/0007164 A1 | 1/2002 | Boggs et al. |
| 2002/0009940 A1 | 1/2002 | May et al. |
| 2002/0019616 A1 | 2/2002 | Thomas et al. |
| 2002/0045877 A1 | 4/2002 | Shimada et al. |
| 2002/0138064 A1 | 9/2002 | Datta et al. |
| 2002/0151862 A1 | 10/2002 | Jitoe et al. |
| 2002/0177376 A1 | 11/2002 | Welch et al. |
| 2003/0093055 A1 | 5/2003 | Elfstrom et al. |
| 2003/0109842 A1 | 6/2003 | Louis et al. |
| 2003/0109843 A1 | 6/2003 | Gibbs |
| 2003/0109844 A1 | 6/2003 | Gibbs |
| 2003/0139726 A1 | 7/2003 | Gibbs |
| 2003/0233082 A1 | 12/2003 | Kline et al. |
| 2004/0013943 A1 | 1/2004 | Stoker et al. |
| 2004/0181200 A1 | 9/2004 | Desai et al. |
| 2004/0182499 A1 | 9/2004 | Collier et al. |
| 2004/0193133 A1 | 9/2004 | Desai et al. |
| 2004/0243083 A1 | 12/2004 | Matsuda et al. |

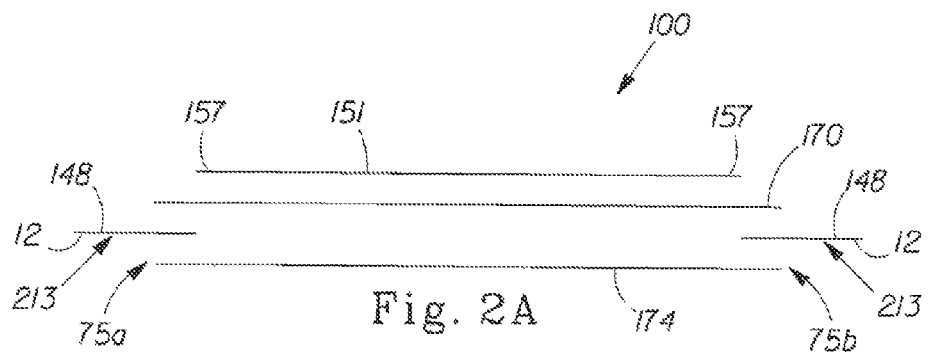
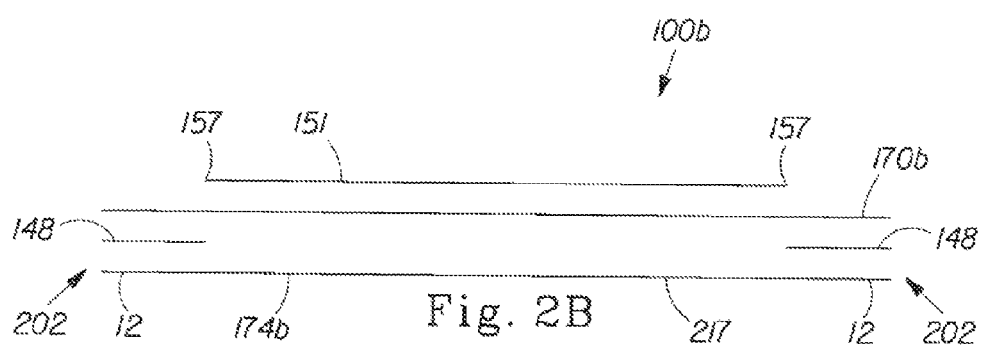
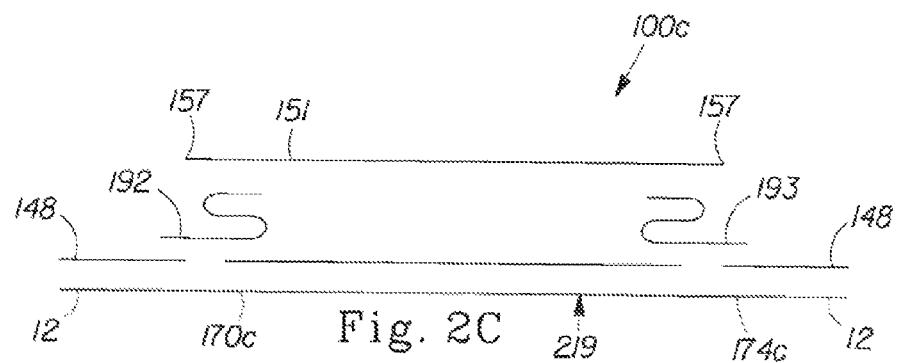

ABSORBENT ARTICLE PROVIDING A BETTER FIT AND MORE COMFORT TO A WEARER

FIELD OF THE INVENTION

The present invention relates to disposable absorbent articles which provide improved wearer comfort, increased leakage protection, and sustained fit. Examples of such disposable absorbent articles include disposable adult incontinence briefs, underwear, pull-on diapers, pants, tape diapers, and disposable panties for menstrual use.

BACKGROUND OF THE INVENTION

It has long been known that absorbent articles such as conventional taped diapers, pull-on diapers, training pants, sanitary napkins, pantiliners, incontinence briefs, and the like, offer the benefit of receiving and containing urine and/or other bodily exudates. For children who are able to walk and who may be engaged in toilet training, the pull-on diaper has become very popular.

Pull-on diapers are generally designed to effectively contain exudates and can be designed to facilitate self-application. Pull-on diapers generally include a front waist region, a back waist region, and a crotch region between the front waist region and the back waist region. Typically, the front waist region and the back waist region can be attached via pairs of side panels to form a waist opening and a pair of leg openings. Pull-on diapers can be manufactured in a pre-joined configuration such that the front and rear waist regions do not need to be attached by a wearer or caregiver prior to donning the article on the wearer.

Typically, pull-on diapers are also designed to provide sustained fit of the pull-on diaper while the wearer moves. For example, in order to prevent the pull-on diaper from sagging or slipping about the waist of the wearer, pull-on diapers may utilize elastic elements in the waist opening and leg openings. The elastic elements in the waist opening can contract the waist opening around the waist of the wearer while the elastic elements in the leg openings can contract the pull-on diaper around the legs of the wearer. However, for many wearers of pull-on diapers, the waist of the wearer may not necessarily be the narrowest portion of the wearer's torso which is covered by the pull-on diaper. A hip region, just below the waist of the wearer, often has a smaller perimeter than the perimeter of the waist of the wearer. In an attempt to maintain the waist opening of the pull-on diaper at the waist of the wearer, most pull-on diapers utilize elastic elements in the waist opening that provide a relatively high contractive force against the waist of the wearer. However, if the waist opening of the pull-on diaper does slip down to the hip region, the smaller perimeter of the hip region can reduce the contractive force applied by the elastic elements in the waist opening thereby making the pull-on diaper more susceptible to sagging or slipping on the wearer.

Unfortunately, the relatively high contractive force of the elastic elements in the waist opening may tend to mark the skin of the wearer. Additionally, this problem may be exacerbated if the elastic elements utilize thin elastic members which can increase localized forces against the waist of the wearer.

Another problem is that a high contractive force in an elastic element in the waist opening can make the pull-on diaper difficult to apply for either the caregiver or the wearer. In addition, for pull-on diapers which are refastenable, an elastic element in the waist opening with a relatively high contractive force may give the caregiver a false perception that the pull-on diaper is too small for the wearer.

Other pull-on diapers, may position elastic strands across the front waist region, back waist region, and a portion of the crotch region, of the pull-on diaper in order to prevent the pull-on diaper from sagging or slipping about the waist of the wearer. However, while these additional elastic strands may contract the front and back waist regions of the pull-on diaper, they can also contract a portion of the crotch region of the pull-on diaper. The contracting of the portion of the crotch region may cause the absorbent core to be gathered and bunched in the crotch region. Unfortunately, this gathering and bunching of the absorbent core can result in a higher risk of leakage from the pull-on diaper. Moreover, this gathering of the absorbent core can also detrimentally affect the aesthetic appeal and comfort of the pull-on diaper.

Consequently, a need exists for a disposable pull-on garment which facilitates donning the pull-on garment on a wearer while still providing sustained fit. There is also a need for a disposable pull-on garment which reduces the possibility of leakage from the disposable pull-on garment while providing sustained fit.

SUMMARY OF THE INVENTION

Disposable absorbent articles constructed in accordance with the present invention can allow for easier donning of the article on a wearer and provide sustained fit and greater comfort for the wearer. A disposable absorbent article for wearing about the lower torso of a wearer comprises a front waist region, a back waist region, a crotch region disposed between the front and back waist regions; a front waist edge and a back waist edge; and a first longitudinal edge and a second longitudinal edge. The disposable absorbent article further comprises a chassis which includes a topsheet, a backsheet attached to at least a portion of the topsheet, and an absorbent core disposed between the topsheet and the backsheet.

The disposable absorbent article further comprises a front waist member attached to the chassis between the first longitudinal edge and the second longitudinal edge adjacent to the front waist edge, wherein the front waist member has a first retraction force. A back waist member is attached to the chassis between the first longitudinal edge and the second longitudinal edge adjacent to the back waist edge, wherein the back waist member has a second retraction force.

The disposable absorbent article further comprises a pair of side panels. Each of the pair of side panels has a waist zone and a hip zone, wherein the waist zones have retraction forces which are about equal to the first retraction force, and the hip zones have a retraction forces which are greater than the first or second retraction forces. Each of the pair of side panels is attached to the chassis such that the waist zones are disposed proximate to the front waist edge or the back waist edge.

In one embodiment, the disposable absorbent article may be a pant. In this embodiment, the pant may comprise a pair of front side panels, one extending from the first longitudinal edge and the other extending from the second longitudinal edge in the front waist region, wherein each of the first pair of side panels comprises a first waist zone and a first hip zone. Also included are a pair of back side panels, one extending from the first longitudinal edge and the other extending from the second longitudinal edge in the back waist region, wherein each of the pair of back side panels comprises a second waist zone and a second hip zone. The pair of front side panels is attached to the pair of back side panels, thereby forming a waist opening and a pair of leg openings.

In this embodiment, the first waist zones can have retraction forces which are about equal to the first retraction force, and the second waist zones can have retraction forces which are about equal to the second retraction force. The first hip zones and the second hip zones can have retraction forces which are greater than the first and second retraction forces.

BRIEF DESCRIPTION OF THE DRAWINGS

FIG. 2A is an exploded cross sectional view showing the pant of FIG. 1B as seen through section line 2A-2A.

FIGS. 2B-2D are exaggerated cross sectional views showing other embodiments of pants constructed in accordance with the present invention.

DETAILED DESCRIPTION OF THE INVENTION

Definitions

Figure 1A:
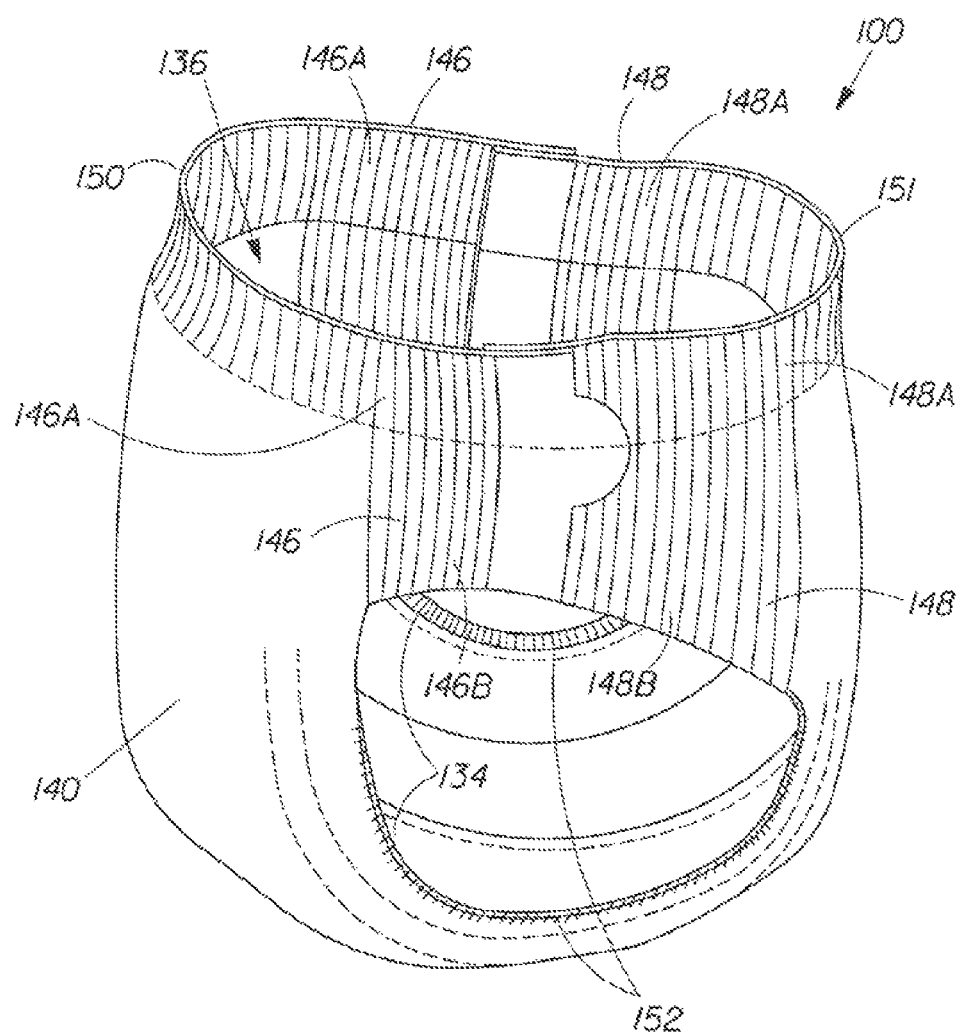
FIG. 1A shows a pant constructed in accordance with the present invention.

As used herein, the following terms have the following meanings.

As used herein, the term "absorbent article" refers to devices that absorb and contain body exudates and, more specifically, refers to devices that are placed against or in proximity to the body of a wearer to absorb and contain the various exudates discharged from the body.

The term "attached" refers to elements being connected or united by fastening, adhering, bonding, etc. by any method suitable for the elements being fastened, secured, or joined, together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The term "disposable" is used herein to describe absorbent articles that generally are not intended to be laundered or otherwise restored or reused as absorbent articles (i.e., they are intended to be discarded after a single use and, preferably, to be recycled, composted or otherwise discarded in an environmentally compatible manner).

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

The term "longitudinal" refers to a direction running from one waist edge of the article to an opposing waist edge of the article and generally parallel to a line which corresponds to the maximum linear dimension of the article. Directions within ±45° of the longitudinal direction are considered to be "longitudinal".

The term "lateral" refers to a direction running from one side edge of the article to an opposing side edge of the article and generally at a right angle to the longitudinal direction and in the same plane as the longitudinal direction. Directions within ±45° of the lateral direction are considered to be "lateral".

The terms "pant", "training pant", "closed diaper", "prefastened diaper", and "pull-on diaper" as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

The term "retraction force" as used herein refers to a measured value obtained via a two cycle hysteresis test, which is described herein, at a strain of 50% on a second downward cycle.

Description

Disposable absorbent articles constructed in accordance with the present invention can facilitate donning the absorbent article on a wearer while providing sustained fit. Moreover, disposable absorbent articles constructed in accordance with the present invention maintain sustained fit without increasing the likelihood of leakage from the disposable absorbent article.

As shown in FIG. 1A, a pull-on diaper 100 constructed in accordance with the present invention may comprise a chassis 140, front side panels 146, and back side panels 148. Note that the front side panels 146 and the back side panels 148 can be elastically extensible. As shown, the pull-on diaper 100 is in a pre-fastened configuration and further comprises a waist opening 136 and a pair of leg openings 134.

The chassis 140 may comprise elastic leg features 152, a front waist member 150, and a back waist member 151. The elastic leg features 152 can allow the leg openings 134 to expand and contract about the legs of a wearer, thereby allowing the pull-on diaper 100 to fit a wide variety of wearers with varying size legs. The front waist member 150 and the back waist member 151 can allow the waist opening 136 to expand and contract about the waist of a wearer, thereby allowing the pull-on diaper 100 to fit a wide variety of wearers with varying waist sizes.

Front side panels 146 may comprise first waist zones 146A, and the back side panels 148 may comprise second waist zones 148A. Also, the front side panels 146 may further comprise first hip zones 146B, and the back side panels 148 may further comprise second hip zones 148B. The first waist zones 146A can have retraction forces which are about equal to the retraction force of the front waist member 150. Similarly, the second waist zones 148A can have retraction forces which are about equal to the back waist member 151. Thus, in a pre-fastened configuration, as shown, the front waist member 150 and the back waist member 151, in combination with the first and the second waist zones 146A and 148A can effectively create a waistband which surrounds the perimeter of the waist of the wearer, thereby providing the pull-on diaper 100 with a more comfortable and better fit. Moreover, the first and the second hip zones 146B and 148B can have retraction forces which are higher than those of the front waist member 150, the back waist member 151, and the first and the second waist zones 146A and 148A.

A benefit of the lower retraction forces in the front waist member 150, the back waist member 151, and the first and the second waist zones 146A and 148A, as opposed to an elastic element in a waist opening which has a higher retraction force, is that the waist opening 136 of the pull-on diaper 100 can expand with less force. Thus, lower retraction forces in the front waist member 150, back waist member 151, and the first and the second waist zones 146A and 148A, of the pull-on diaper 100, can facilitate donning the pull-on diaper 100 on the wearer. Additionally, the higher retraction force in the first and the second hip zones 146B and 148B can provide sustained fit of the pull-on diaper while on the wearer and can ensure that the pull-on diaper 100 does not slip or sag on the wearer.

Figure 1B:
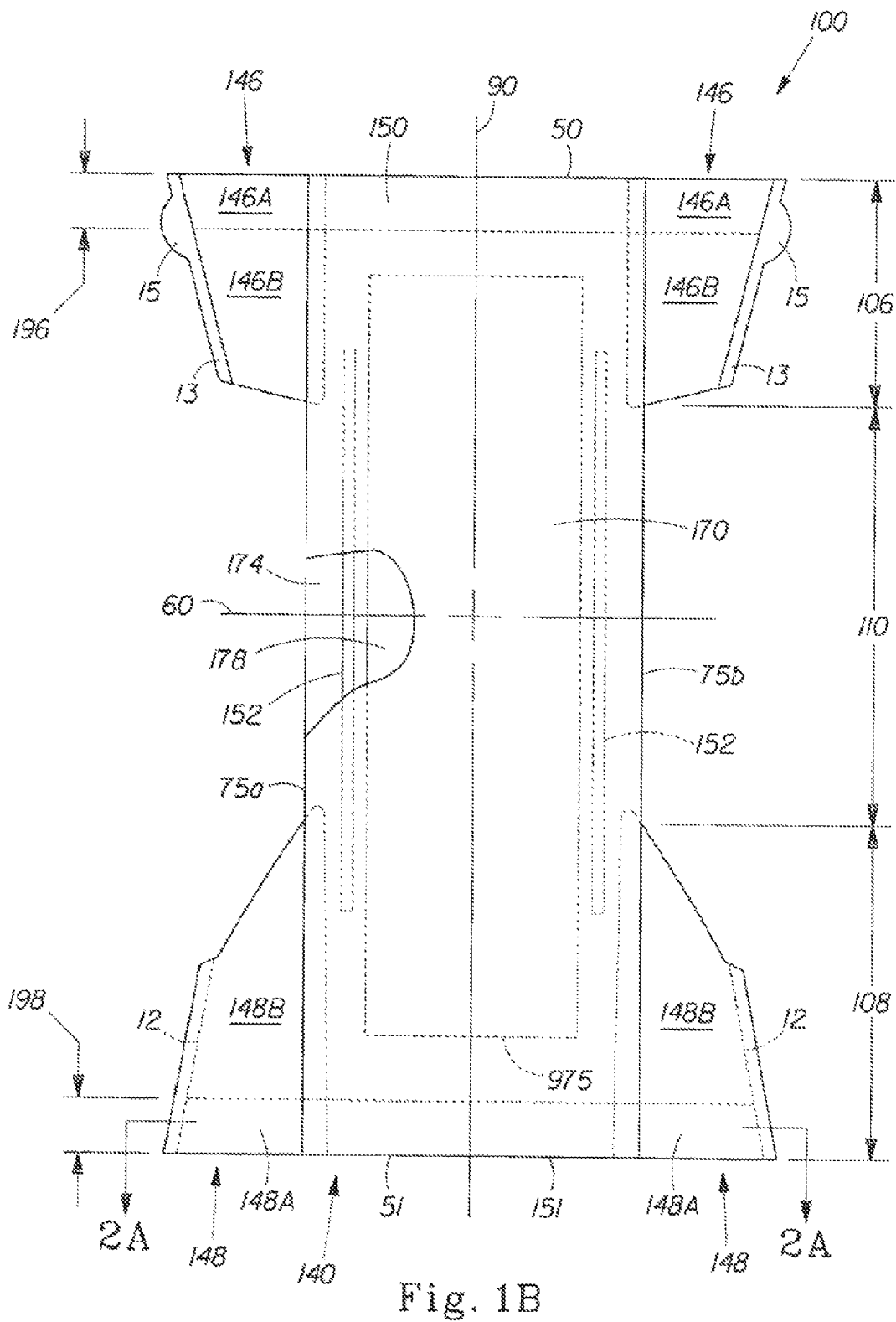
FIG. 1B is a partial cut-away view showing the pant of FIG. 1A in a flat, uncontracted state (i.e., without elastic induced contraction).

FIG. 1B is a plan view of the pull-on diaper 100 in a flattened, uncontracted state with portions of the structure being cut-away to more clearly show the construction of the pull-on diaper 100. As shown, the portion of the pull-on diaper 100 that faces a wearer is oriented towards the viewer. As stated previously, the pull-on diaper 100 may comprise the chassis 140, a front waist region 106, a back waist region 108, and a crotch region 110 disposed between the front waist region 106 and the back waist region 108. The chassis 140 may further comprise a topsheet 170, a backsheet 174, and an absorbent core 178. The absorbent core 178 can be positioned between at least a portion of the topsheet 170 and the backsheet 174.

The periphery of the chassis 140 can be defined by the longitudinal edges 75a and 75b, a front waist edge 50, and a back waist edge 51. The longitudinal edges 75a and 75b run generally parallel to a longitudinal centerline 90 of the pull-on diaper 100. The front waist edge 50 and the back waist edge 51 run generally parallel to a lateral centerline 60 of the pull-on diaper 100.

As shown, the elastic leg features 152 can be disposed adjacent to the longitudinal edges 75a and 75b. Also, the front waist member 150 can be disposed adjacent to the front waist edge 50 in the front waist region 106 while the back waist member 151 can be disposed adjacent to the back waist edge 51 in the back waist region 108. The front waist member 150 and the back waist member 151 can be of any length, including extending from one longitudinal edge 75a to the other longitudinal edge 75b in the front waist region 106 and the back waist region 108, respectively.

The front side panels 146 can extend outboard from the longitudinal edges 75a and 75b of the chassis 140 in the front waist region 106. The back side panels 148 can extend outboard from longitudinal edges 75a and 75b of the chassis 140 in the back waist region 108. The front side panels 146 can attach to the back side panels 148 via front attachment elements 13 and back attachment elements 12 to form the waist opening and the leg opening of the pull-on diaper 100. The front side panels 146 and the back side panels 148 can be attached to the chassis 140 such that the first and the second waist zones 146A and 148A are disposed proximate to the front waist edge 50 and the back waist edge 51, respectively.

At least one of the front side panels 146 may comprise a tab 15 which may facilitate the attachment of the front attachment element 13 to the back attachment element 12. Also, the tab 15 may facilitate the unfastening of the front attachment element 13 from the back attachment element 12. Similarly, the back side panels 148 may also comprise a tab either as an alternative to or in conjunction with the tab 15 of the front side panels 146.

As stated previously, each of the first and the second waist zones 146A and 148A, the first and the second hip zones 146B and 148B, front waist member 150, and back waist member 151, have a retraction force. Also, as stated previously, in one embodiment, the first waist zones 146A can have retraction forces which are about equal to the retraction force of the front waist member 150 while the second waist zones 148A can have retraction forces which are about equal to the retraction force of the back waist member 151. In one embodiment, the retraction force of the front waist member 150 is less than that of the back waist member 151. Also, in this embodiment, the first and the second hip zones 146B and 148B may have higher retraction forces than the back waist member 151. Alternatively, the retraction force of the first waist member 150 can be about equal to the retraction force of the back waist member 151.

The front waist member 150 and the first waist zones 146A can have a first length 196 ranging from about 10 mm to about 50 mm. The back waist member 151 and the second waist zones 148A can have a second length 198 which is within the range of the first length 196. In order to reduce the likelihood of marking the skin of the wearer, each of the first and the second waist zones 146A and 148A, and front and back waist members 150 and 151, can have a length equal to that of the first and second lengths 196 and 198 which minimize localized forces exerted on the waist of the wearer. In another embodiment, the second length 198 is less than or equal to about the first length 196. In yet another embodiment, the second length 198 is greater than or equal to about the first length 196.

As shown, the front waist member 150 and the back waist member 151 can be positioned on chassis 140 such that they do not overlap ends 975 of the absorbent core 178. Because the front waist member 150 and the back waist members 151 can be positioned such that they do not overlap the ends 975 of the absorbent core 178, the front waist member 150 and the back waist member 151 do not gather the absorbent core 178.

In one embodiment, the first and the second waist zones 146A and 148A, the front waist member 150, and the back waist member 151, can have retraction forces which range from about 30 grams force/inch (11.8 grams force/cm) to about 70 grams force/inch (27.5 grams force/cm). In yet another embodiment, the first and the second waist zones 146A and 148A, the front waist member 150, and the back waist member 151, can have retraction forces which range from about 30 grams force/inch (11.8 grams force/cm) to less than about 85 grams force/inch (33.4 grams force/cm). In another embodiment, the first and the second waist zones 146A and 148A, the front waist member 150, and the back waist member 151, can have retraction forces which are less than or equal to about 27.5 grams force/cm. In yet another embodiment, the first and the second hip zones 146B and 148B can have retraction forces which are greater than or equal to about 85 grams force/inch (33.4 grams force/cm).

FIG. 2A is an exaggerated cross sectional view showing the pull-on diaper 100 through section line 2A-2A in the back waist region (item 108, see FIG. 1B). As shown, the back waist member 151 can be disposed on the topsheet 170 between the longitudinal edges 75a and 75b. Alternatively, the back waist member 151 can be positioned such that ends 157 of the back waist member 151 do no overlap any portion of the back side panels 148. The back side panels 148 can be disposed between the topsheet 170 and the backsheet 174 and can be attached to the topsheet 170, the backsheet 174, or both. The back side panels 148 can extend outboard of the longitudinal edges 75a and 75b and can also have a portion inboard of the longitudinal edges 75a and 75b which is attached to the backsheet 174 or the topsheet 170. Note that the back attachment elements 12 can be disposed on an underside 213 of the back side panels 148.

FIG. 2B is an exaggerated cross sectional view showing a pull-on diaper 100b which is constructed in accordance with the present invention. Similar to the cross section shown in FIG. 2A, the back waist member 151 can be disposed on a portion of a topsheet 170b. As shown, the back waist member 151 can be positioned such that ends 157 of the back waist member 151 do not overlap any portion of the back side panels 148. Also, the back side panels 148 can be disposed between the topsheet 170b and a backsheet 174b. However, the topsheet 170b and the backsheet 174b can extend to an outer edge 202 of the back side panels 148 and be generally coextensive with the back side panels 148. Note that the back attachment elements 12 can be disposed on an underside 217 of the backsheet 174b.

FIG. 2C is an exaggerated cross sectional view showing a pull-on diaper 100c which is constructed in accordance with the present invention. As shown, the back waist member 151 can be disposed over a portion of a topsheet 170c. The back waist member 151 can also be disposed over portions of barrier leg cuffs 192 and 193. As shown, the back waist member 151 can be positioned such that ends 157 of the back waist member 151 do not overlap any portion of the back side panels 148. Similar to the cross section shown in FIG. 2A, the back side panels 148 can be attached to a backsheet 174c and the topsheet 170c. However, the back side panels 148 can also be attached to the barrier leg cuffs 192 and 193. Note that the back attachment elements 12 can be disposed on an underside 219 of the backsheet 174c.

Figure 2D:
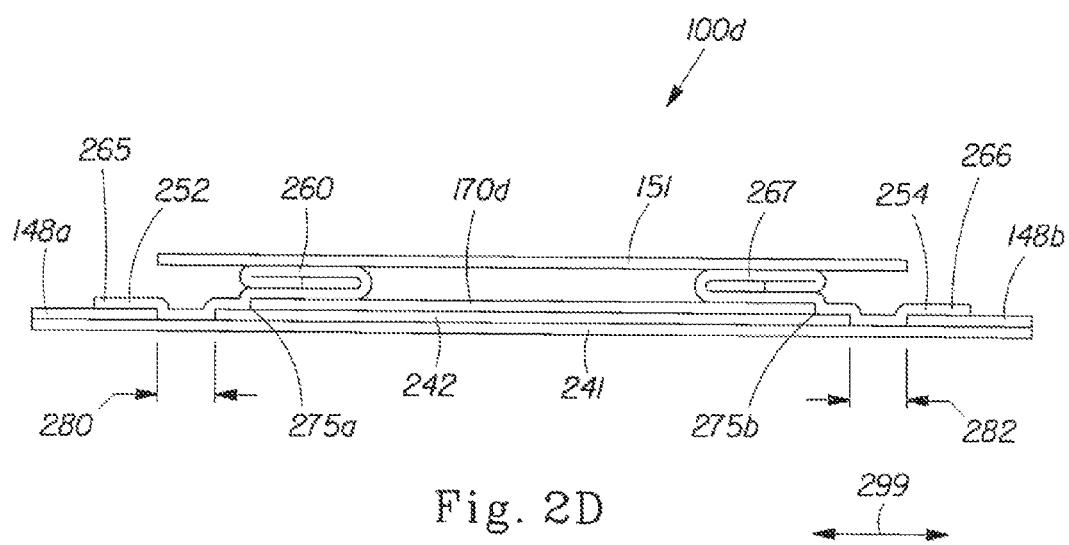

FIG. 2D is an exaggerated cross sectional view showing a pull-on diaper 100d which is constructed in accordance with the present invention. The pull-on diaper 100d may comprise at least two barrier leg cuffs 252 and 254 attached to a topsheet 170d along a pair of longitudinal edges 275a and 275b and attached to a first backsheet layer 241. (The leg cuffs can be and are sometimes also referred to as leg bands, side flaps, leg cuffs, barrier cuff, elastic cuffs, or gasketing cuffs.)

The barrier leg cuff 252 comprises a distal end 260 and a proximal end 265 while the barrier leg cuff 254 comprises a distal end 267 and a proximal end 266. The proximal end 265 of the barrier leg cuff 252 can be attached to a side panel 148a and the first backsheet layer 241 in an overlapping manner. Similarly, the proximal end 266 of the barrier leg cuff 254 can be attached to a side panel 148b and the first backsheet layer 241 in an overlapping manner. The distal end 260 of the barrier leg cuff 252 can be attached to the topsheet 170d and a second backsheet layer 242. Similarly, the distal end 267 of the barrier leg cuff 254 can be attached to the topsheet 170d and the second backsheet layer 242.

As shown, the barrier leg cuffs 252 and 254 can be attached to the first backsheet layer 241 in between their attachment to the side panels 148a and 148b, respectively, and the second backsheet layer 242 such that a first gap 280 and a second gap 282 are created. The first gap 280 can extend longitudinally for a length of the side panel 148a. Similarly, the second gap 282 can extend longitudinally for a length of the side panel 148b. The first gap 280 can define a width of a non-elastic region of the pull-on diaper 100d disposed between the side panel 148a and the second backsheet layer 242, and the second gap 282 can define a width of a non-elastic region of the pull-on diaper 100d disposed between the side panel 148b and the second backsheet layer 242.

Both the first and second gaps 280 and 282 may be of any suitable nonzero width in a lateral direction 299. For example, in one embodiment, both the first and the second gaps 280 and 282 may range in width from about 0.5 mm to about 26 mm. In another embodiment, the first and the second gaps 280 and 282 may range in width from about 0.5 mm to about 20 mm. In yet another embodiment, the first and the second gaps 280 and 282 may range in width from about 1 mm to about 15 mm.

The pull-on diaper 100d may further comprise the back waist member 151 which may be disposed on the distal end 260 of the barrier leg cuff 252 and the distal end 267 of the barrier leg cuff 254. The back waist member 151 may transcend both the longitudinal edges 275a and 275b such that the back waist member 151 overlaps a portion of the first gap 280 and the second gap 282. In addition, the back waist member 151 may overlap a portion of the side panel 148a and a portion of the side panel 148b. In another embodiment, the back waist member 151 does not overlap a portion of the side panel 148a or the side panel 148b. In yet another embodiment, the back waist member 151 does not overlap any portion of the first gap 280 or the second gap 282.

The barrier leg cuffs of FIGS. 2C and 2D can provide improved containment of liquids and other body exudates. In addition, these barrier leg cuffs may include several different embodiments for reducing the leakage of body exudates in the leg regions. Illustrative examples of suitable barrier leg cuffs for use in the present invention may be found in U.S. Pat. No. 3,860,003 entitled "Contractable Side Portions for Disposable Diaper" issued to Buell on Jan. 14, 1975; U.S. Pat. No. 4,909,803 entitled "Disposable Absorbent Article Having Elasticized Flaps" issued to Aziz et al. on Mar. 20, 1990; U.S. Pat. No. 4,695,278 entitled "Absorbent Article Having Dual Cuffs" issued to Lawson on Sep. 22, 1987; U.S. Pat. No. 4,795,454 entitled "Absorbent Article Having Leakage-Resistant Dual Cuffs" issued to Dragoo on Jan. 3, 1989; and U.S. Pat. No. 4,704,115 entitled "Disposable Waist Containment Garment" issued to Buell on Nov. 3, 1987.

Note, that the barrier leg cuffs of FIGS. 2C and 2D may be attached to a pull-on diaper, as described above, by any suitable attachment means or combinations of attachment means known in the art. Some examples of suitable attachment means include, but are not limited to, adhesive bonds, heat bonds, pressure bonds, ultrasonic bonds, and dynamic mechanical bonds.

As discussed above, the front waist member and the back waist member may be disposed in the pull-on diaper in a number of different configurations, including configurations similar to those shown in FIGS. 2A-2D. Other suitable configurations for both the front waist member and the back waist member are described in U.S. Pat. No. 4,515,595, U.S. Pat. No. 4,710,189, U.S. Pat. No. 5,151,092, and U.S. Pat. No. 5,221,274.

Note that a pull-on diaper constructed in accordance with the present invention may comprise front side panels and back side panels which include more than two zones of elasticity. For example, a leg zone may be added to the front side panels and back side panels discussed above. The additional leg zone is discussed hereafter with regard to FIG. 3.

Figure 3:
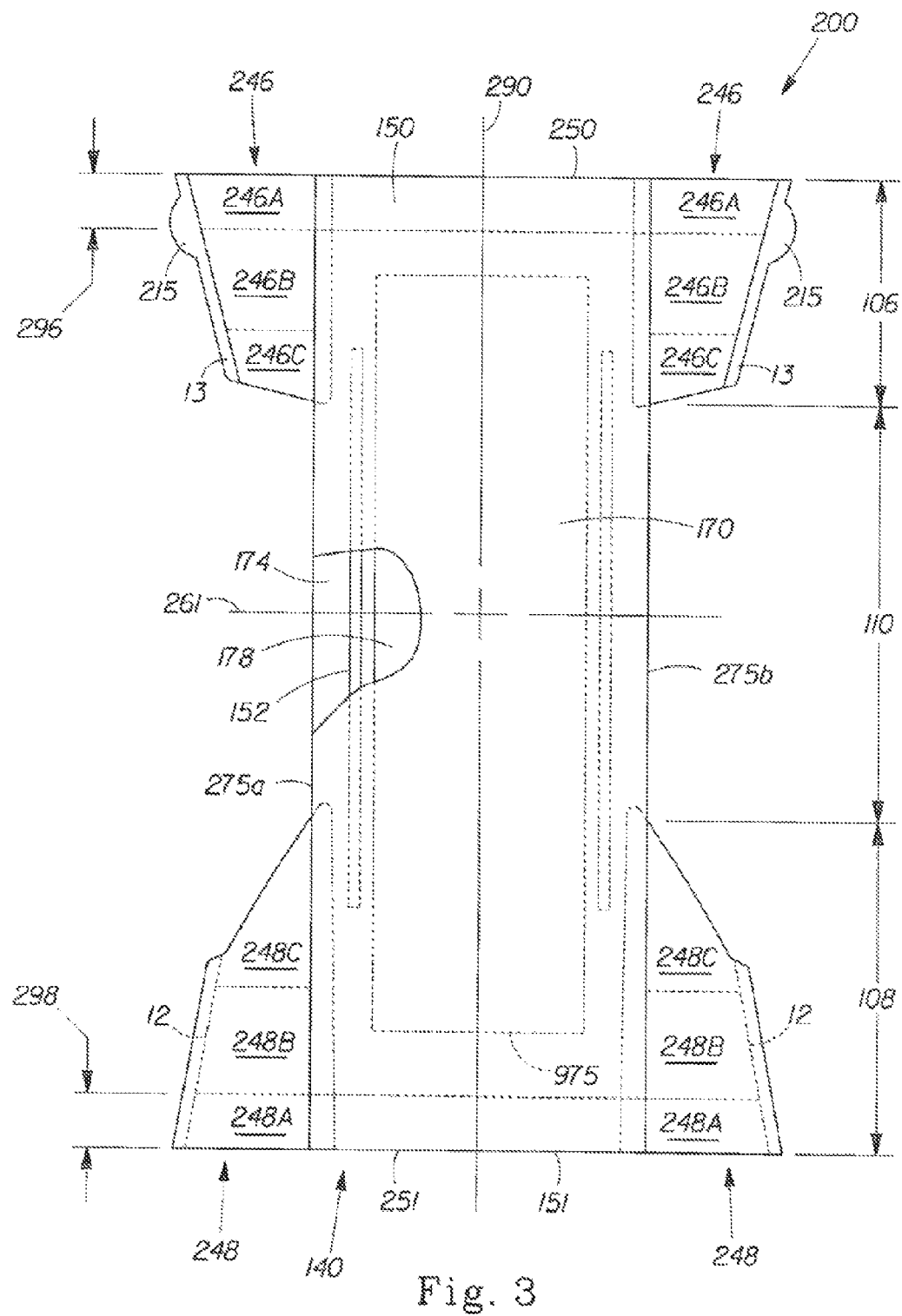
FIG. 3 is a partial cut-away view showing a pant constructed in accordance with the present invention, the pant is shown in a flat, uncontracted state (i.e., without elastic induced contraction).

FIG. 3 is a plan view of a pull-on diaper 200 in a flattened, uncontracted state with portions of the structure being cutaway to more clearly show the construction of the pull-on diaper 200. The portion of the pull-on diaper 200 that faces a wearer is oriented towards the viewer. Also, the pull-on diaper 200 is constructed in accordance with the present invention.

The pull-on diaper 200 may comprise the chassis 140 of the pull-on diaper 100 (see FIG. 1B). The periphery of the chassis 140 can be defined by longitudinal edges 1075a and 1075b, a front waist edge 250, and a back waist edge 251. The longitudinal edges 1075a and 1075b run generally parallel to a longitudinal centerline 290 of the pull-on diaper 200. The front waist edge 250 and the back waist edge 251 run generally parallel to a lateral centerline 261 of the pull-on diaper 200.

The pull-on diaper 200 may further comprise front side panels 246 and the back side panels 248 which are elastically extensible. As shown the front side panels 246 and the back side panels 248 extend outboard from the longitudinal edges 1075a and 1075b of the chassis 140. Each of the front side panels 246 may comprise first waist zones 246A, first hip zones 246B, and first leg zones 246C, and the back side panels 248 may comprise second waist zones 248A, second hip zones 248B, and second leg zones 248C.

The retraction forces of the first and the second waist zones 246A and 248A and the first and the second hip zones 246B and 248B can be similar to the forces described in regard to waist zones and hip zones of FIGS. 1A and 1B. The first and the second leg zones 246C and 248C can have retraction forces which are less than the retraction forces of the first and the second hip zones 246B and 248B. Also, the retraction forces of the first and the second waist zones 246A and 248A can be less than or equal to the retraction forces in the first and the second leg zones 246C and 248C. The first and the second leg zones 246C and 248C can have retraction forces which range from about 30 grams force/inch (11.8 grams force/cm) to less than about 85 grams force/inch (33.4 grams force/cm). In another embodiment, the first and the second leg zones 246C and 248C can have retraction forces which range from about 45 grams force/inch (17.7 grams force/cm) to about 80 grams force/inch (31.5 grams force/cm).

Similar to the pull-on diaper 100 (see FIG. 1B), the pull-on diaper 200 may further comprise front attachment elements 13 and back attachment elements 12 which can be attached to the front side panels 246 and the back side panels 248, respectively. Moreover, one of the front side panels 246 may comprise a tab 215 which may facilitate the attachment of the front attachment element 13 to the back attachment element 12. Also, note that the cross sections shown in FIGS. 2A-2C for the pull-on diaper 100 are equally applicable for the pull-on diaper 200.

The lengths of the various zones in the pull-on diaper 200 may vary. In one embodiment, the first waist zones 246A and front waist member 150 can have a first length 296 ranging from about 10 mm to about 50 mm. The second waist zones 248A and back waist member 151 can have a second length 298 which is similar to the first length 296. In order to reduce the likelihood of marking the skin of the wearer, the waist zones 246A and 248A, can have a first and second lengths 296 and 298 which reduce localized forces exerted on the waist of the wearer. In another embodiment, the second length 298 is less than or equal to about the first length 296. In yet another embodiment, the second length 298 is greater than or equal to about the first length 296. In yet another embodiment, the first and the second hip zones 246B and 248B can have a length of about 10 mm to about 60 mm. Also, in this embodiment, the first and the second leg zones 246C and 248C can have length of about 10 mm to about 70 mm.

Note that although the embodiments shown in FIGS. 1A, 1B, and 3, depict front side panels and back side panels, a pull-on diaper constructed in accordance with the present invention can comprise a pair of front side panels extending outboard from a chassis in a front waist region, wherein the front side panels can attach to the back waist region. In another embodiment, a pull-on diaper constructed in accordance with the present invention may comprise a pair of back side panels extending outboard from a chassis in a back waist region, herein the back side panels can attach to the front waist region. In yet another embodiment, a pull-on diaper constructed in accordance with the present invention may comprise a pair of side panels one of which extends outboard from a chassis in a front waist region and the other of which extends outboard from the chassis in the back waist region. Moreover, note that the embodiments discussed herein are equally applicable to disposable absorbent articles which are fastened about a waist of a wearer as opposed to being pulled on the wearer.

As discussed previously, the side panels, both front and back, used in the present invention may each comprise a plurality of zones having different retraction forces. The side panels of the present invention may further comprise an elastic element and a substrate which is attached to the elastic element such that the side panel is laminated. Typically, any elastic element in any side panel does not extend from one longitudinal edge of a chassis to another longitudinal edge of the chassis. The elastic element of the side panel may overlap a portion of a single longitudinal edge of the chassis.

The side panels of the present invention can form a portion of a leg opening when the absorbent article, which the side panels are a part of, is fastened. The side panels of the present invention form a portion of the leg opening which would be disposed on an outer surface of a leg of a wearer. A crotch region of a chassis in conjunction with a first waist region and a second waist region can form a portion of the leg opening which would be disposed on an inner surface of the leg of the wearer.

Furthermore, both the first waist region and the second waist region can form a portion of a waist opening on a front and rear waist area of the wearer. In contrast, the side panels can form a portion of the waist opening on a hip area of the wearer.

The constituents of the side panel are but one of the factors which determine an effective method of providing the side panel with a retraction force in one zone which is either higher or lower than a retraction force in another zone. Examples of side panels which can have a retraction force in one zone and a higher or lower retraction force in another and methods of forming the same are provided below.

Figure 4A:
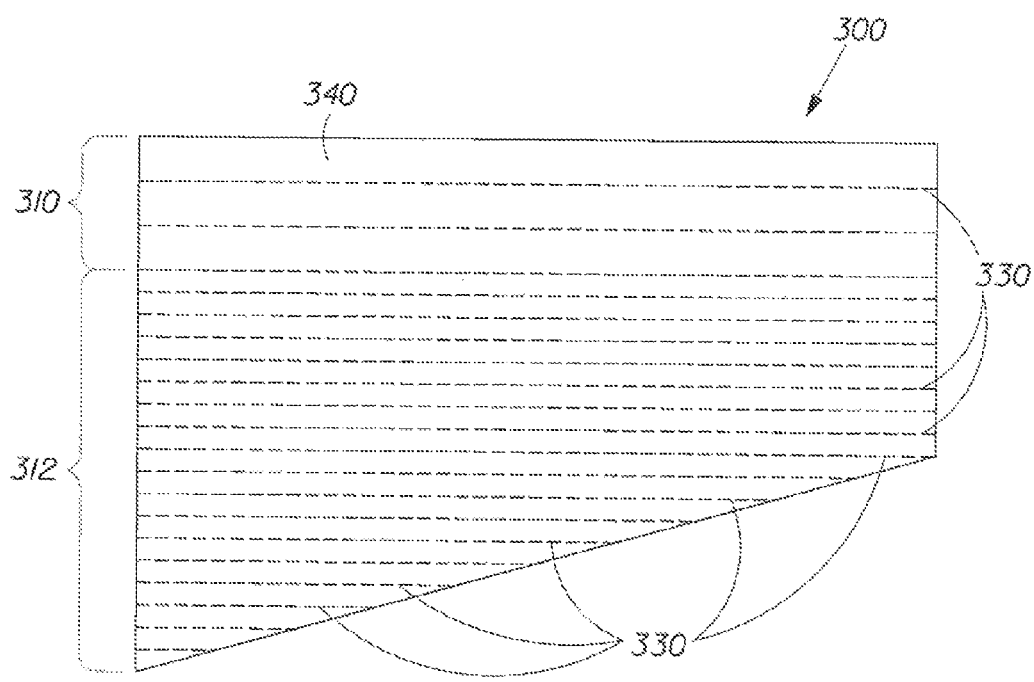
FIGS. 4A-4C show side panels constructed in accordance with the present invention.

As shown in FIG. 4A, in one embodiment, a side panel 300 may comprise an elastic element which includes a plurality of elastic elements 330 attached to a substrate 340. The side panel 300 can have a waist zone 310 with a first retraction force and a hip zone 312 with a higher second retraction force by altering the spacing of the plurality of elastic elements 330. For example, the spacing between each of the plurality of elastic elements 330 in the waist zone 310 may be about 2 mm while the spacing between each of the plurality of elastic elements 330 in the hip zone 312 may be about 1 mm. Assuming the plurality of elastic elements 330 has the same physical and chemical properties in the waist zone 310 and the hip zone 312, the hip zone 312 can have a higher retraction force than the waist zone 310. Note that a similar method may be utilized to provide the side panel with more than two zones which have differing retraction forces.

In another embodiment, the variability of retraction forces can be accomplished by altering the properties of a plurality of elastic elements. For example, a plurality of elastic elements in a waist zone can have different physical or chemical properties from a plurality of elastic elements in a hip zone as discussed in regard to FIG. 4B.

Figure 4B:
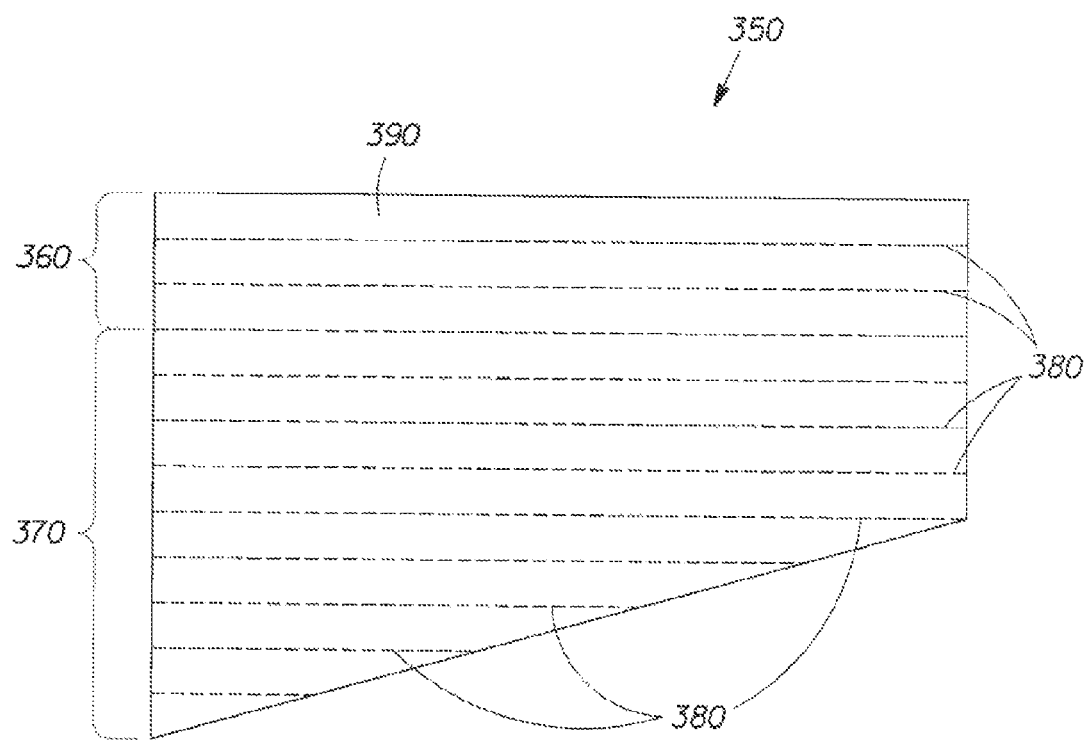

As shown in FIG. 4B, a side panel 350 may comprise a plurality of elastic elements 380 which are attached to a substrate 390. Adjacent elements of the plurality of elastic elements 380 can be approximately equally spaced apart; however, adjacent strands of the plurality of elastic elements are not required to be approximately equally spaced apart. In order to provide the side panel 350 with varying retraction forces, the plurality of elastic elements 380 in a waist zone 360 may have a smaller cross sectional area than a cross sectional area of the plurality of elastic elements 380 in a hip zone 370. For example, where the elastic elements comprise elastic strands, the cross sectional area of the plurality of elastic elements in the waist zone 360 can vary from about 0.03 mm$^2$ to about 0.1 mm$^2$. In contrast, the cross sectional area of the plurality of elastic elements in the hip zone 370 can be greater than about 0.1 mm$^2$ and less than or equal to about 0.4 mm$^2$, thereby providing the hip zone 370 with a higher retraction force. In another example, where the elastic elements comprise elastic films, the thickness of the plurality of elastic element in the waist zone 360 can vary from about 1 mil to about 6 mils.

Figure 4C:
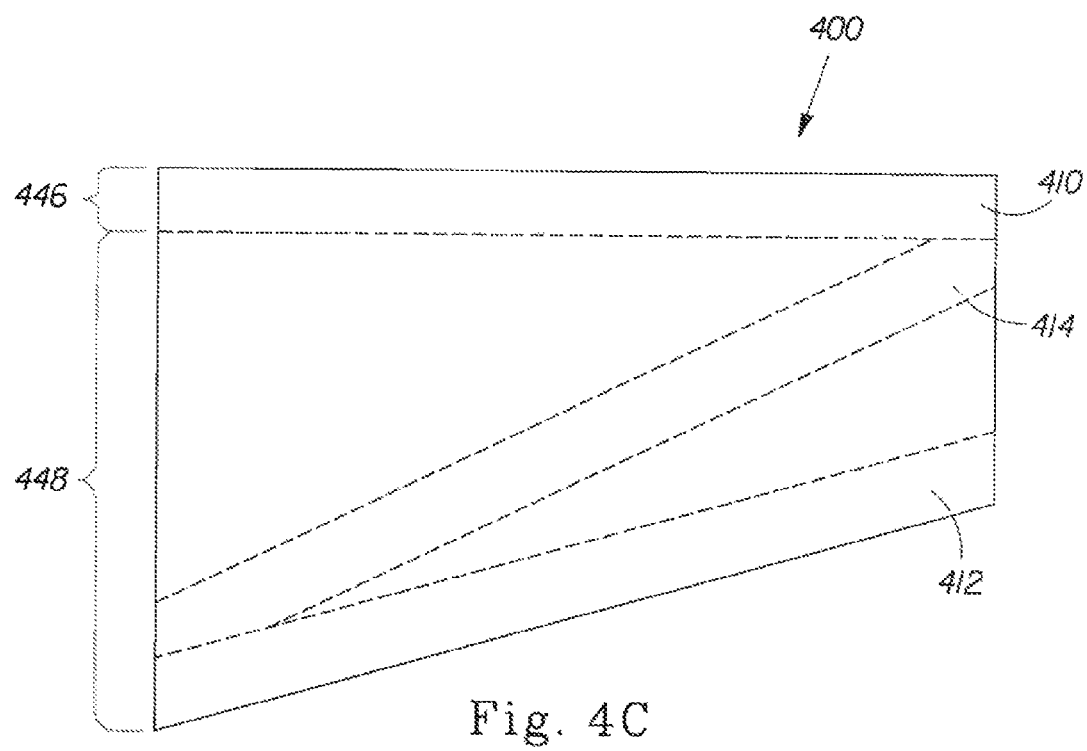

As shown in FIG. 4C, a side panel 400 may comprise a first elastic element 410, a second elastic element 412, and a third elastic element 414 attached to a substrate. The first elastic element 410 can be disposed in a waist zone 446 while the second and third elastic elements 412 and 414 can be disposed in a hip zone 448. The third elastic element 414 can extend from the second elastic element 412 to the first elastic element 410. The presence of the third elastic element 414 can cause the hip zone 448 to have a higher retraction force than the retraction force of the waist zone 446.

In another embodiment, the variability of retraction forces can be accomplished by mechanically activating portions of the side panel to different percentages of strain. A side panel can be mechanically activated by meshing the side panel between first and second activation rolls each of which comprise a plurality of teeth. The teeth of the first activation roll can intermesh with the teeth of the second activation roll. The percentage strain experienced by the side panel can be determined by the depth of engagement (depth to which the teeth of the first activation roll intermesh with the teeth of the second activation roll) of the teeth of the first and second activation rolls. For portions of the side panel that have been activated, it may be possible to achieve a higher retraction force at smaller depths of engagement, e.g. smaller teeth. However, smaller depths of engagement or smaller percentages of strain can lead to a laminated structure which is less elastically extensible. For example, a side panel which was strained to 200% may be able to elastically extend up to about three times its original length. However, a side panel which was strained to 500% may be able to elastically extend up to about six times its original length.

In another embodiment, the variability of retraction forces can be accomplished by providing a zone with additional elastic elements. For example, an additional elastic element or elements may be added to the hip zone of the side panel. In another example, a side panel may comprise an elastic element which is present in both a waist zone and a hip zone. In order to increase the retraction force in the hip zone, an additional elastic element may be added to the hip zone such that the retraction force of the hip zone is increased with respect to the waist zone. Note that any of the above methods for can be combined to provide the desired properties in a side panel.

An elastic element of the present invention may include elastic strands or elastic films. Any suitable elastic film known in the art can be used. Suitable elastic films may comprise polypropylene, polyethylene, polyolefins, styrene-isoprene-styrene, styrene-butadiene-styrene, or combinations thereof. The gage thickness of the elastic films was discussed previously. The basis weight of the films can range from about 10 gsm to about 100 gsm.

Alternatively, or in conjunction with the elastic film, an elastic element of the present invention may comprise elastic strands. Suitable elastic strands can be made of a resilient elastic thermoplastic material. The elastic strands may be made from liquid elastic that is extruded through a die to achieve the desired strand elastic diameter and/or shape. The shape of the extruded elastic strands is not limited. For example, typical elastic strands have a circular cross sectional shape, but sometimes the elastic strands may have different shapes, such as a trilobal shape, or a flat (i.e., "ribbon" like) shape. Suitable elastic strand shapes include rectangles, circles, ellipses, diamonds, triangles, parallelograms, trapezoids, wedges or other sections of circles or ellipses, other polygons, or other irregular enclosed shapes. Furthermore, the thickness or diameter of the elastic strands may vary in order to accommodate a particular application. Typically, the thickness of elastic strands may be in the range of about 0.02 mm to about 1 mm and the basis weight is in the range of about 20 g/m$^2$ to about 300 g/m$^2$.

The elastic strands may be applied separately to the substrate, can be extruded onto the substrate, or can be printed onto the substrate. Suitable apparatuses for applying elastic strands onto a substrate or extruding a elastic strands onto a substrate are discussed below. Apparatuses for applying elastic strands in a longitudinal direction are described in U.S. Application No. 2004/0238105 A1 and in U.S. application Ser. No. 10/836,944 entitled "Apparatus for Producing Elastomeric Nonwoven Laminates" filed on Apr. 30, 2004. Apparatuses for applying elastic strands in a transverse direction, an angle from the longitudinal direction, or in a curvilinear fashion are described in U.S. application Ser. No. 10/779,338 entitled "Method of Placing Material Transversely on a Moving Web" filed on Feb. 13, 2004. Apparatuses for applying elastic strands in the longitudinal direction, an angle from the longitudinal direction, or in a curvilinear fashion are described in U.S. application Ser. No. 10/834,539 entitled "Extrusion Applicator Having Linear Motion Operability" filed on Apr. 29, 2004, and in U.S. application Ser. No. 10/834,503 entitled "Extrusion Applicator Having Rotational Operability" filed on Apr. 29, 2004.

Suitable apparatuses and methods for printing elastic elements in any orientation are described in U.S. application Ser. No. 10/811,671 entitled "Variable Stretch Composites and Methods of Making the Composite" filed on Mar. 29, 2004, and in U.S. application Ser. No. 10/811,527 entitled "Variable Stretch Composites and Methods of Making the Composite" filed on Mar. 29, 2004. For the printing of elastic strands, the individual elastic strands may be configured as lines or strands generally having widths less than about 2 mm and typically less than about 1 mm. Linear elastic strands may be configured as bands generally having widths between about 2 mm and about 20 mm and aspect ratios ranging from about 2:1 to about 100:1. Typically, the thickness of an elastic strand may be in the range of about 0.02 mm to about 5 mm and the basis weight is in the range of about 20 g/m² to about 300 g/m².

As discussed previously, the side panels utilized in the present invention may comprise laminated structures. In one embodiment, a side panel comprises a laminated structure which includes a first substrate and a second substrate attached to an elastic element. The first substrate and the second substrate are attached to the elastic element in a face to face orientation such that the elastic layer is sandwiched between the first substrate and the second substrate.

The first or second substrates may comprise woven materials, nonwoven materials, combinations of woven and nonwoven materials, or laminated structures having woven or nonwoven materials. Suitable nonwoven materials for use in accordance with the present invention may comprise fibers made of polypropylene, polyethylene, polyester, nylon, cellulose, polyamide, or combinations of such materials. Fibers of one material or fibers of different materials or material combinations may be used in the nonwovens. Suitable processes for manufacturing nonwoven materials include spunbond, spunbond meltblown spunbond (SMS), spunbond meltblown meltblown spunbond (SMMS), carded and the like. Other suitable nonwoven materials include high elongation carded (HEC) nonwovens and deep activation polypropylene (DAPP) nonwovens. Any process known in the art may be used to make the nonwovens.

If a nonwoven is used, the nonwoven may comprise fibers that are bonded internally, including fibers that are needle punched, hydro entangled, spunbonded, thermally bonded, bonded by various types of chemical bonding such as latex bonding, powder bonding, and the like. The basis weight of the first nonwoven and/or second nonwoven may, for example, be in the range of about 10 gsm to about 40 gsm.

The first substrate, second substrate and the elastic layer may be attached by any means of attachment known in the art. Some examples of suitable attaching means and/or methods for attaching include, but are not limited to, adhesives, cohesives, thermal bonding, pressure bonding, mechanical bonding, ultrasonic bonding, and/or any combination of any known methods of attaching such materials.

As discussed previously, front side panels can attach to back side panels or to a chassis such that a waist opening and a pair of leg openings are formed. The front side panels may be attached to the back side panels or the chassis in a non-refastenable manner. Alternatively, the front side panels may be attached to the back side panels or chassis in a refastenable manner. The front side panels may attach to the back side panels or chassis in a number of different ways. For example, suitable attachment means may utilize adhesives, cohesives, mechanical means, or any combination thereof. In one embodiment, the front side panels may attach to the back side panels via a tab and slot fastener. In another embodiment, the front side panels may be attached to the back side panels via hook and loop or hook and hook type fasteners. Any other means known in the art for attaching the front side panels to the back side panels or chassis may be used with the present invention. Similarly, the back side panels may attach to the chassis utilizing any of the attachment means described above. Some suitable examples of fastening systems which may be utilized in the present invention are disclosed in U.S. Pat. No. 3,848,594; U.S. Pat. No. 4,662,875; U.S. Pat. No. 4,846,815; U.S. Pat. No. 4,894,060; U.S. Pat. No. 4,946,527; U.S. Pat. No. 5,151,092; U.S. Pat. No. 5,221,274; and U.S. Pat. No. 6,432,098.

The disposable absorbent article of the present invention, as discussed previously, comprises many different elements, e.g. a topsheet, a backsheet, an absorbent core, etc. A wide assortment of materials can be used for the different elements of the pull-on garment as discussed herein. For example, any topsheet compatible with the present invention which is known in the art can be used in the present invention. A suitable material for a topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. As an example, a material suitable for use in a topsheet comprises a web of staple-length polypropylene fibers is manufactured by Veratec, Inc., a Division of International Paper Company, of Walpole, Mass. under the designation P-8.

Some examples of suitable topsheets are described further in U.S. Pat. No. 3,929,135; U.S. Pat. No. 4,324,246; U.S. Pat. No. 4,342,314; U.S. Pat. No. 4,463,045; U.S. Pat. No. 5,006,394; U.S. Pat. No. 4,609,518; U.S. Pat. No. 4,629,643. Any portion of the topsheet may be coated with a lotion as is known in the art. Examples of suitable lotions include those described in U.S. Pat. No. 5,607,760; U.S. Pat. No. 5,609,587; U.S. Pat. No. 5,635,191; U.S. Pat. No. 5,643,588; U.S. Pat. No. 5,968,025; U.S. Pat. No. 6,716,441; and PCT Publication No. WO 95/24173.

Further, the topsheet may be fully or partially elasticated or may be foreshortened so as to provide a void space between the topsheet and the absorbent core. Exemplary structures including elasticized or foreshortened topsheets are described in more detail in U.S. Pat. No. 4,892,536; U.S. Pat. No. 4,990,147; U.S. Pat. No. 5,037,416; and U.S. Pat. No. 5,269,775.

A suitable backsheet for use in the disposable absorbent article of the present invention may comprise a laminated structure. For example, as previously discussed, the backsheet may comprise a first backsheet layer and a second backsheet layer (see items 241 and 242 of FIG. 2D). The second backsheet layer can be impervious to liquids (e.g., urine) and comprise a thin plastic film such as a thermoplastic film having a thickness, for example, of about 0.012 mm (0.5 mil) to about 0.051 mm (2.0 mils). Suitable backsheet films include those manufactured by Tredegar Corporation, based in Richmond, Va., and sold under the trade name CPC2 film. Either the first backsheet layer or the second backsheet layer may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. No. 5,938,648; U.S. Pat. No. 5,865,823; and 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Suitable absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147,345; U.S. Pat. No. 5,342,338; U.S. Pat. No. 5,260,345; U.S. Pat. No. 5,387,207; and U.S. Pat. No. 5,625,222.

The backsheet may be attached to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. No. 4,573,986; U.S. Pat. No. 3,911,173; U.S. Pat. No. 4,785,996; and U.S. Pat. No. 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on garment or may be one or more separate elements attached directly or indirectly with one or more elements of the disposable absorbent article. Further, the sublayer may include a structure that is separate from the absorbent core or may include or be part of at least a portion of the absorbent core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. No. 6,680,422 and U.S. Pat. No. 5,941,864. Further, the sublayer, or any portion thereof, may include or be coated with a lotion or other known substances to add, enhance or change the performance or other characteristics of the element.

The disposable absorbent article may further comprise leg cuffs which provide improved containment of liquids and other body exudates. Leg cuffs may also be referred to as leg bands, side flaps, barrier cuffs, or elastic cuffs. Examples of leg cuffs which can be utilized in the pull-on garment of the present invention are provided in U.S. Pat. No. 3,860,003; U.S. Pat. No. 4,808,178; U.S. Pat. No. 4,909,803; U.S. Pat. No. 4,695,278; and U.S. Pat. No. 4,795,454. In some embodiments, it may be desirable to treat all or a portion of the leg cuffs with a lotion or fecal modification agent which either increases or decreases the Hardness of fecal material which it encounters.

Embodiments of the present invention may also include pockets for receiving and containing waste, spacers which provide voids for waste, barriers for limiting the movement of waste in the article, compartments or voids which accept and contain waste materials deposited in the pull-on garment, and the like, or any combinations thereof. Examples of pockets and spacers for use in absorbent products are described in U.S. Pat. No. 5,514,121; U.S. Pat. No. 5,171,236; U.S. Pat. No. 5,397,318; U.S. Pat. No. 5,540,671; U.S. Pat. No. 6,168,584; U.S. Pat. No. 5,306,266; and U.S. Pat. No. 5,997,520. Examples of compartments or voids in an absorbent article are disclosed in U.S. Pat. No. 4,968,312; U.S. Pat. No. 4,990,147; U.S. Pat. No. 5,062,840; and U.S. Pat. No. 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. No. 5,941,864; U.S. Pat. No. 5,977,430; and U.S. Pat. No. 6,013,063.

Embodiments of the present invention may include acquisition layers and dusting layers, each of which are well known in the art. Acquisition layer are further discussed in U.S. Pat. No. 5,460,622. Dusting layers are further discussed in U.S. Pat. No. 4,888,231.

Test Methods:

The test method for determining the retraction force of a portion of an absorbent article is provided below.

Required Equipment:

1. A tensile testing machine available from Instron Engineering Corp. of Canton, Mass.

available under the model #'s 4200, 4300, 4500, or 5500, series is used. Note that the tensile tester is interfaced with a computer loaded with the Instron® Merlin™ Material Testing Software which controls the testing parameters, performs data acquisition and calculation, and provides graphs and data reports.

2. Select a load cell such that the forces measured will be between 20% and 80% of the capacity of the load cell or the load range used. The load cell is also selected such that the load cell meets the specification of ASTM E-4.

3. Light duty jaws are used on the tensile tester and are wider than the sample. Typically, 2.54 cm (1") wide rubber coated face contact grips are used. The grips are air-actuated and designed to concentrate the entire gripping force along a plane perpendicular to the direction of testing stress. The air pressure of the pneumatic grips is set to 60 psi.

4. A precision ruler which is traceable to the National Bureau of Standards is used.

5. A pair of scissors or other cutting instrument is used.

All of the steps involved in the sample preparation and the testing of the samples, unless otherwise noted, are performed in a controlled environment of 23.0° C.±1.0° C. and a relative humidity of 50%±2.0%. All samples prepared are allowed to equilibrate in this controlled environment of a period of two hours prior to testing.

Preparation of Equipment:
1. Calibrate the tensile tester according to the manufacturer's instructions.
2. Set the gauge length of the tensile tester to 20 mm
3. Set the tensile tester crosshead to move at 508 mm/minute.
4. Set the Merlin™ Material Testing Software, discussed above, to mark a load at a first cycle in grams-force, a load at a second cycle in grams-force, and a load at 50% strain during the second cycle in a down direction in grams-force.
5. The tensile tester is set to go through the following steps during the testing of a sample.
   a. Perform a 5.0 gram pre-load at a crosshead speed of 12.7 mm/min
   b. Pull the sample to 200.0% elongation, i.e. (sample should be 3 times its original length). Hold this elongation for 30 seconds.
   c. Return sample to 0% elongation and hold for 60 seconds.
   d. Repeat step b.
   e. Return sample to 0% elongation.

Figure 5:
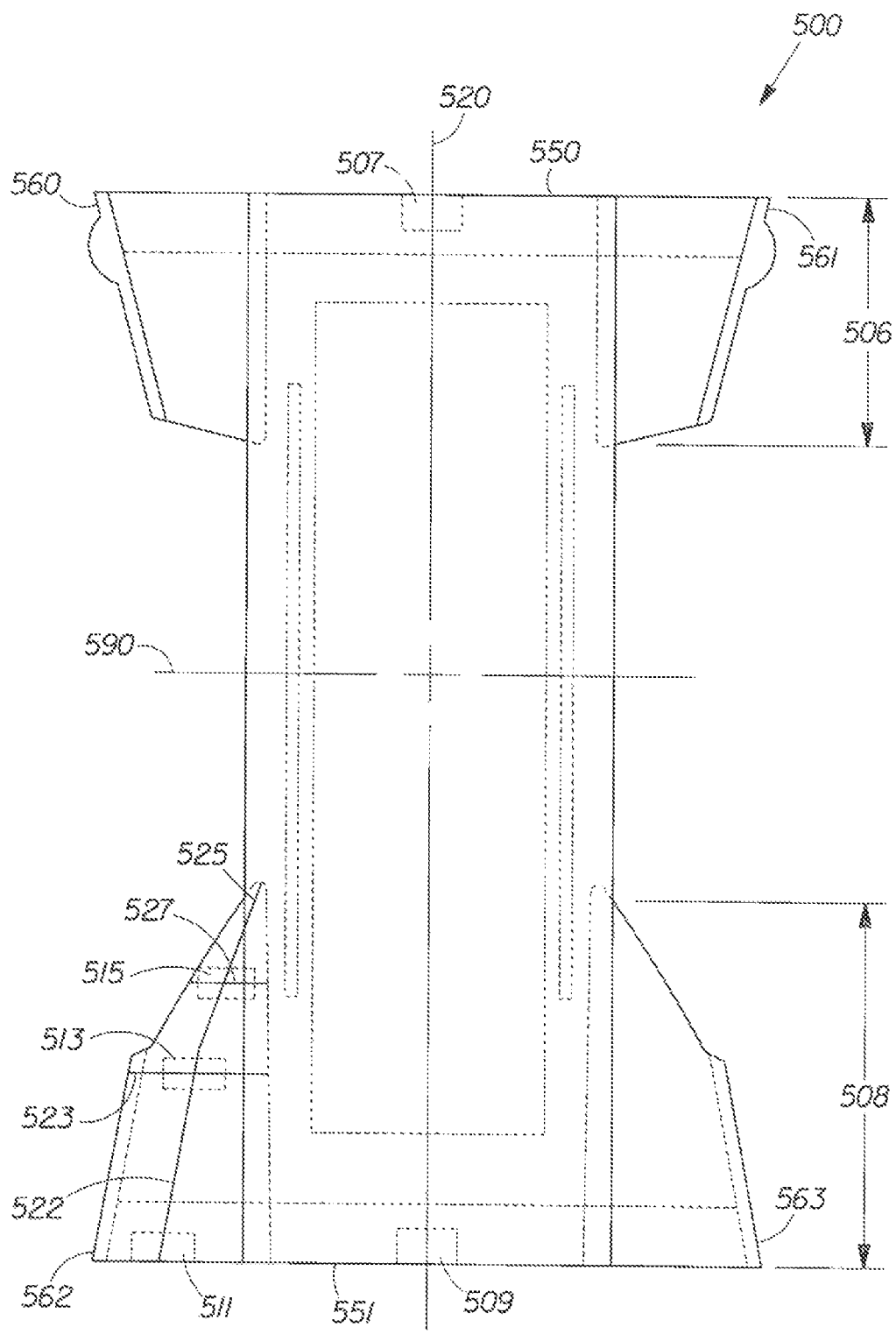
FIG. 5 is a plan view of a disposable absorbent article showing a plurality of sample locations for testing purposes.

Sample Preparation:

Regarding FIG. 5, the gauge length of the samples provided below runs generally parallel to a lateral centerline 590 of a disposable absorbent article 500.
1. Enough representative absorbent articles are selected from the retail packaging of the absorbent article to conduct all required tests.
2. As shown in FIG. 5, samples are prepared from the disposable absorbent article 500. A front waist sample 507, a back waist sample 509, a waist zone sample 511, and a hip zone sample 513 are created. Note that all samples are created from their respective absorbent articles while the absorbent articles are in the relaxed state. Also note that more than one waist zone sample and one hip zone sample may need to be created.
4. Make a first mark 520 which is parallel to a longitudinal axis of the disposable absorbent article 500. The first mark 520 is drawn such that a front waist edge 550 and a back waist edge 551 are bisected (cut into two equal parts) by the first mark 520. Note that the front waist edge 550 extends from a first outer edge 560 to a second outer edge 561. Similarly, the back waist edge 551 extends from a third outer edge 562 to a fourth outer edge 563.
5. Locate a lateral centerline 590 for the disposable absorbent article 500.
6. Cut out the front waist sample 507 from a front waist region 506. The front waist sample 507 has a gauge length of 20 mm and a longitudinal dimension of 10 mm. The first mark 520 bisects the gauge length of the front waist sample 507. The longitudinal dimension begins from the front waist edge 550.
7. Cut out the back waist sample 509 from a back waist region 508. The back waist sample 509 has a gauge length of 20 mm and a longitudinal dimension of 10 mm. The first mark 520 bisects the gauge length of the back waist sample 509. The longitudinal dimension begins from the back waist edge 551.
8. Locate an inner edge 525 of an elastic member of a side panel. If the elastic member comprises a plurality of elastic strands, the inner edge 525 is an average interior end point for the plurality of elastic strands.
9. Locate an outer edge of the elastic member of a side panel. For example, the elastic member may be coterminous with a substrate of the side panel along the outer edge. For example, the third outer edge 562, as previously defined, can be used as the outer edge in some instances.
10. Make a second mark 522 on the side panel such that a distance between the inner edge 525 and the third outer edge 562 along the back waist edge 551 is bisected. The second mark 522 bisects the distance between the inner edge 525 and the third outer edge 562 for the longitudinal length of the inner edge 525.
11. Cut out the waist zone sample 511 which has a gauge length of 20 mm and a longitudinal dimension of 10 mm. The second mark 522 bisects the gauge length of the waist zone sample 511. The longitudinal dimension begins from the back waist edge 551.
12. Make a third mark 523 parallel to the lateral centerline 590 which extends from the third outer edge 562 to the inner edge 525 and bisects the inner edge 525.
13. Cut out a hip zone sample 513 which has a gauge length of 20 mm and a longitudinal dimension of 10 mm. The second mark 522 bisects the gauge length while the third mark 523 bisects the longitudinal dimension.
14. If the sample population includes a leg zone as discussed previously in regard to FIG. 3, then measure a distance 70 mm from the back waist edge 551 along the inner edge 525. Make a fourth mark 527 parallel to the lateral centerline 590 from the inner edge 525 at a point on the inner edge 525 which is 70 mm from the back waist edge 551 to the third outer edge 562.
15. Cut out a leg zone sample 515 which has a gauge length of 20 mm and a longitudinal dimension of 10 mm. The second mark 522 bisects the gauge length while the fourth mark 527 bisects the longitudinal dimension.
16. Repeat steps 8 through 15 for all side panels included on the absorbent article 500 substituting the front waist edge 550 for the back waist edge 551 where necessary.

Testing of the Samples:
1. Mount one end of the sample to be tested in the bottom jaw, and mount the other end of the sample to be tested into the top jaw.
2. Start the tensile tester and data collection devices simultaneously as described by the manufacturer's instructions. Data is collected throughout the testing.
3. When the tensile tester has completed step 5e from the Preparation of Equipment section, remove the sample from the tensile tester.
4. Return the crosshead of the tensile tester to the starting position in preparation for the next sample.
5. Repeat steps 1-4 for all of the samples which need to be tested.
6. Analyze data to determine the load at 50% strain in the downward direction of the second cycle.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing about the lower torso of a wearer, the disposable absorbent article comprising: a front waist region, a back waist region, a crotch region disposed between the front and back waist regions; a front waist edge and a back waist edge; and a first longitudinal edge and a second longitudinal edge; the disposable absorbent article further comprising:
    a chassis comprising:
        a topsheet;
        a backsheet attached to at least a portion of the topsheet; and
        an absorbent core disposed between the topsheet and the backsheet;
    a front waist member attached to the chassis between the first longitudinal edge and the second longitudinal edge adjacent to the front waist edge, wherein the front waist member has a first retraction force;
    a back waist member attached to the chassis between the first longitudinal edge and the second longitudinal edge adjacent to the back waist edge, wherein the back waist member has a second retraction force;
    a pair of side panels each having a waist zone and a hip zone, wherein the waist zone has retraction forces which are about equal to the first retraction force, wherein the hip zone has retraction forces which are greater than the first or second retraction forces, wherein the pair of side panels are attached to the chassis such that waist zone is disposed proximate to the front waist edge or the back waist edge, and wherein each side panel comprises an attachment element to attach the side panels to one another through refastenable bonds.

2. The disposable absorbent article of claim 1, wherein the first retraction force is about equal to the second retraction force.

3. The disposable absorbent article of claim 1, wherein the second retraction force is greater than the first retraction force.

4. The disposable absorbent article of claim 1, wherein the first retraction force and the second retraction force range from about 11.8 grams force/cm to less than about 33.4 grams force/cm.

5. The disposable absorbent article of claim 1, wherein the retraction force of the hip zone is greater than or equal to about 33.4 grams force/cm.

6. The disposable absorbent article of claim 1, wherein the first retraction force and the second retraction force are about equal to 27.5 grams force/cm.

7. The disposable absorbent article of claim 1, wherein at least one of the pair of side panels comprises a plurality of elastic elements sandwiched between a first and a second substrate.

8. The disposable absorbent article of claim 7, wherein the plurality of elastic elements in the waist zone has a first distance between adjacent elastic elements and the plurality of elastic elements in the hip zone has a second distance between adjacent elastic elements, and wherein the first distance is greater than the second distance.

9. The disposable absorbent article of claim 7, wherein the plurality of elastic elements in the waist zone has a first cross sectional area and the plurality of elastic elements in the hip zone has a second cross sectional area, and wherein the second cross sectional area is greater than the first cross sectional area.

10. The disposable absorbent article of claim 1, wherein at least one of the pair of side panels further comprises a leg zone, wherein the hip zone is disposed between the waist zone and the leg zone.

11. The disposable absorbent article of claim 10, wherein the leg zone has a leg retraction force which ranges from about 11.8 grams force/cm to less than about 33.4 grams force/cm.

12. The disposable absorbent article of claim 1, wherein at least one of the side panels comprises a tab to facilitate the attachment of the attachment elements.

13. A disposable pant for wearing about the lower torso of a wearer, the disposable pant comprising: a front waist region, a back waist region, a crotch region disposed between the front and back waist regions; a front waist edge and a back waist edge; and a first longitudinal edge and a second longitudinal edge; the disposable pant further comprising:
    a chassis comprising:
        a topsheet;
        a backsheet attached to at least a portion of the topsheet;
        an absorbent core disposed between the topsheet and the backsheet;
    a front waist member attached to the chassis, the front waist member extending from the first longitudinal edge to the second longitudinal edge adjacent to the front waist edge, wherein the front waist member has a first retraction force;
    a back waist member attached to the chassis, the back waist member extending from the first longitudinal edge to the second longitudinal edge adjacent to the back waist edge, wherein the back waist member has a second retraction force;
    a pair of front side panels, one extending from the first longitudinal edge in the front waist region and the other extending from the second longitudinal edge in the front waist region, wherein each of the first pair of side panels comprises a first waist zone and a first hip zone; and
    a pair of back side panels, one extending from the first longitudinal edge in the back waist region and the other extending from the second longitudinal edge in the back waist region, wherein each of the pair of back side panels comprises a second waist zone and a second hip zone,
    wherein the first waist zone has retraction forces which are about equal to the first retraction force, wherein the second waist zone has retraction forces which are about equal to the second retraction force, wherein the first hip zone and the second hip zone have retraction forces which are greater than the first and second retraction forces, and wherein the pair of front side panels are attached to the pair of back side panels through refastenable bonds, thereby forming a waist opening and a pair of leg openings.

14. The disposable pant of claim 13, wherein the first retraction force is about equal to the second retraction force.

15. The disposable pant of claim 13, wherein the second retraction force is greater than the first retraction force.

16. The disposable pant of claim 13, wherein the first retraction force and the second retraction force range from about 11.8 grams force/cm to less than about 33.4 grams force/cm.

17. The disposable pant of claim 16, wherein the retraction forces of the first and second hip zones are greater than or equal to about 33.4 grams force/cm.

18. The disposable pant of claim 13, wherein the first retraction force and the second retraction force are about equal to 27.5 grams force/cm.

19. The disposable pant of claim 13, wherein each of the front side panels and the back side panels comprise a plurality of elastic elements sandwiched between a first and a second substrate, wherein the plurality of elastic elements in the first and second waist zones have a first distance between adjacent elastic elements and the plurality of elastic elements in the first and second hip zones have a second distance between adjacent elastic elements, and wherein the first distance is greater than the second distance.

20. The disposable pant of claim 13, wherein each of the front side panels and the back side panels comprise a plurality of elastic elements sandwiched between a first and a second substrate, wherein the plurality of elastic elements in the first and second waist zones have a first cross sectional area and the plurality of elastic elements in the first and second hip zones have a second cross sectional area, and wherein the second cross sectional area is greater than the first cross sectional area.

21. The disposable pant of claim 13, wherein each of the front side panels further comprise a first leg zone disposed adjacent to the leg openings such that the first hip zone is disposed between the first waist zone and the first leg zone, wherein each of the back side panels further comprise a second leg zone disposed adjacent to the leg openings such that the second hip zone is disposed between the second waist zones and the second leg zones, and wherein the first and the second leg zones have leg retraction forces which range from about 11.8 grams force/cm to less than about 33.4 grams force/cm.

22. The disposable pant of claim 13, wherein at least one of the front side panels comprises a tab to facilitate attachment of the refastenable bonds.

* * * * *